US008822438B2

(12) United States Patent
Auerbach et al.

(10) Patent No.: US 8,822,438 B2
(45) Date of Patent: Sep. 2, 2014

(54) METHODS AND COMPOSITIONS FOR TREATING CANCER

(75) Inventors: Alan H. Auerbach, Hermosa Beach, CA (US); Arie S. Belldegrum, Los Angeles, CA (US)

(73) Assignee: Janssen Oncology, Inc., Los Angeles, CA (US)

( * ) Notice: Subject to any disclaimer, the term of this patent is extended or adjusted under 35 U.S.C. 154(b) by 0 days.

(21) Appl. No.: 13/034,340

(22) Filed: Feb. 24, 2011

(65) Prior Publication Data

US 2011/0144016 A1  Jun. 16, 2011

Related U.S. Application Data

(63) Continuation of application No. 11/844,440, filed on Aug. 24, 2007, now abandoned.

(60) Provisional application No. 60/921,506, filed on Aug. 25, 2006.

(51) Int. Cl.
*A61K 31/56* (2006.01)
*A61K 31/58* (2006.01)

(52) U.S. Cl.
CPC .................................... *A61K 31/58* (2013.01)
USPC ........................................ 514/170; 514/180

(58) Field of Classification Search
USPC ................................................. 514/170, 182
See application file for complete search history.

(56) References Cited

U.S. PATENT DOCUMENTS

2006/0030608 A1   2/2006  Nelson et al.

FOREIGN PATENT DOCUMENTS

| EP | 2478907    | 7/2012 |
| WO | 2006027266 | 3/2006 |

OTHER PUBLICATIONS

O'Donnell et al., British Journal of Cancer, 2004;90:2317-2325.*
Tannock et al., J. Clin. Oncol., 1996;14:1 756-1764.*
ASCO Cancer Foundation, Poster Session F: Hormone Refractory, ASCO, 2005.
Bruno et al, Targeting cytochrome P450 enzymes: A new approach in anti-cancer drug development, Elsevier, 2007, pp. 5047-5060, vol. 15.
Cannell, 100th Annual Meeting of the American Association for Cancer Research, Los Angeles, CA, USA;, http://oncology.thelancet.com, 2007, pp. 471, vol. 8.
Collins, et al. "A Systematic Review of the effectiveness of Docetaxel and Mitoxantrone for the Treatement of Metastatic Hormone-Refractory Prostate Cancer", British J. of Cancer, 95, pp. 457-462 (2006).
Cougar Biotechnology, Cougar Biotechnology Announces Initiation of Phase I/II Trial for CB7630 (Arbiraterone Acetate), Cougar Biotechnology, Dec. 14, 2004.
Cougar Biotechnology, Cougar Biotechnology Announces Presentation of Positive CB7630 Clinical Data at AACR-NCI-EORTC International Conference on Molecular Targets and Cancer Therapeutics, Cougar Biotechnology, Oct. 2007.
Cougar Biotechnology, Cougar Biotechnology Announces Presentation of Positive CB7630 Clinical Data at ESMO Conference, Drugs.com, Jul. 2007.
Cougar Biotechnology, Cougar Biotechnology announces presentation of positive phase I and phase II data at ASCO Prostate Cancer Symposium, Cougar Biotechnology, Feb. 23, 2007.
Cougar Biotechnology, Cougar Biotechnology presents CB7630 Phase I clinical data at the 2005 Prostate Cancer Symposium, AllBusiness, 2005.
Cougar Biotechnology, Cougar Biotechnology presents positive CB7630 Clinical Data at AACR Annual Meeting Late-Breaking Clinical Trials Session, Cougar Biotechnology, Apr. 17, 2007.
Cougar Biotechnology, Cougar Technology Announces Presentation of Positive CB7630 Clinical Data at ASCO Annual Meeting, The Free Library, Jun. 4, 2007.
De Bono et al, Inhibition of CYP450c17 by abiraterone administered once daily to castrate patients with prostate cancer resistant to LHRH analogues, anti-androgens and steriod therapy is well tolerated . . . , The institute of Cancer Research, 2007.
De Coster, et al., Effects of High-Dose Ketoconazole and Dexamethason on ACTH-Stimulated Adrenal Steriodogenesis in Orchiectomized Prostatic Cancer Patients, ACTA Endocrinologica (Copenh), 1987, pp. 265-271, vol. 115.
Duc et al, In Vitro and in vivo models for the evaluation of potent inhibitors of male rat 17 -hydroxylase/C-lyase, Pergamon, 2003, pp. 537-542, vol. 84.
Endocrinology, Inhibition of Androgen Synthesis in Human Testicular and Prostatic Microsomes and in Male Rats by Novel Steroidal Compounds, Endocrinology, 1999, pp. 2891-2897, vol. 140 No. 6.
Fossa, et al., Weekly Docetaxel and Prednisone Versus Prednisolone Alone in Androgen-Independent Prostate Cancer: A Randomized Phase II Study, European Urology, 2007, pp. 1691-1699, vol. 52.
Gerber, et al., Prostate Specific Antigen for Assessing Response to Ketoconazole and Prednisone in Patients with Hormone Refractory Metastatic Prostate Cancer, The Journal of Urology, 1990, pp. 1177-1179, vol. 1444, No. 5.
Hakki et al, CYP17- and CYP11B-dependent steriod hydroxylases as drug development targets, Elsevier, 2006, pp. 27-52, vol. 11.
Harris, et al., Low Dose Ketoconazole with Replacement Doses of Hydrocortisone in Patients with Progressive Androgen Independent Prostate Cancer, The Journal of Urology, 2002, pp. 542-545, vol. 168.
Moreira et al, Synthesis and evaluation of novel 17-indazole androstene derivatives designed as CYP17 inhibitors, Elsevier, 2007, pp. 939-948, vol. 72.
Newell et al, The Cancer Research UK experience of pre-clinical toxicology studies to support early clinical trials with novel cancer therapies, Elsevier, 2004, pp. 899-906, vol. 40.

(Continued)

*Primary Examiner* — San-Ming Hui

(57) ABSTRACT

Methods and compositions for treating cancer are described herein. More particularly, the methods for treating cancer comprise administering a 17α-hydroxylase/$C_{17,20}$-lyase inhibitor, such as abiraterone acetate (i.e., 3β-acetoxy-17-(3-pyridyl)androsta-5,16-diene), in combination with at least one additional therapeutic agent such as an anti-cancer agent or a steroid. Furthermore, disclosed are compositions comprising a 17α-hydroxylase/$C_{17,20}$-lyase inhibitor, and at least one additional therapeutic agent, such as an anti-cancer agent or a steroid.

20 Claims, No Drawings

(56) References Cited

OTHER PUBLICATIONS

Petrylak, et al., Future Directions in the Treatment of Androgen-Independent Prostate Cancer, Urology, 2005, pp. 8-13, vol. 65, Supplement 6A.
Scholz, et al., Long-Term Outcome for Men with Androgen Independent Prostate Cancer Treated with Ketoconazole and Hydrocortisone, The Journal of Urology, 2005, pp. 1947-1952, vol. 173.
Small et al, The Case for Socondary Hormaonal Therapies in the Chemotherapy Age, The Journal of Urology, 2006, pp. S66-S71, vol. 176.
Wikipedia, Corticosteriod, undated, website, 2013.
Third Party Observations dated Oct. 18, 2012 for EP Appln. No. 07837326.3.
Third Party Observations dated Mar. 28, 2013 for EP Appln. No. 07837326.3.
Third Party Observations dated Jul. 1, 2013 for EP Appln. No. 07837326.3.
Berry, W. et al. Phase III Study of Mitoxantrone Plus Low Dose Prednisone Versus Low Dose Prednisone Alone in Patients with Asymptomatic Hormone Refractory Prostate Cancer, The Journal of Urology, 2002, pp. 2439-2443, vol. 168.
Chang, Ching-Yi, et al. Glucocorticoids Manifest Androgenic Activity in a Cell Derived from a Metastatic Prostate Cancer, Cancer Research, 2001, pp. 8712-8717, vol. 61.
Dorff, TB, Crawford, ED. Management and challenges of corticosteroid therapy in men with metastatic castrate-resistant prostate cancer, Annals of Oncology, 2013, pp. 31-38, vol. 24(1).
Efstathiou, Eleni, et al. Effects of Abiraterone Acetate on Androgen Signaling in Castrate-Resistant Prostate Cancer in Bone, American Society of Clinical Oncology, Journal of Clinical Oncology, 2011, pp. 1-8.
Huggins, Charles, et al. Studies on Prostatic Cancer.I. The Effect of Castration, of Estrogen and of Androgen Injection on Serum Phosphatases in Metastatic Carcinoma of the Prostate, Cancer Research, 1941, pp. 293-297, vol. 1.
Mostaghel, EA. et al. Molecular Pathways: Targeting resistance in the androgen receptor for therapeutic benefit, Clin Cancer Res, Dec. 4, 2013.
Nishimura, Kazuo, et al. Potential Mechanism for the Effects of Dexamethasone on Growth of Androgen-Independent Prostate Cancer, Journal of the National Cancer Institute, 2001, pp. 1739-1746, vol. 93.
Oudar, Stephane, et al. Actualite dans le cancer de la prostate, Synthese, Bull Cancer 2005; 92 (10), pp. 865-873 (relevance in English abstract).
Petrylak, et al. Docetaxel and Estramustine Compared with Mitoxantrone and Prednisone for Advanced Refractory Prostate Cancer, The New England Journal of Medicine, 2004, pp. 1513-1520, vol. 351.
Ryan, et al., Aberaterone Acetate in Metastatic Prostate Cancer Without Previous Chemotherapy, The New England Journal of Medicine, 2013, 368:138-148.
Sartor, et al, Abiraterone Prolongs Survival in Metastatic Prostate Cancer, Nature Reviews Clinical Oncology, 2011, pp. 515-516, vol. 8.
Tannock, IF, et al. Docetaxel plus prednisone or mitoxantrone plus prednisone for advanced prostate cancer, The New England Journal of Medicine, 2004, pp. 1502-1512, vol. 351(15).
Assessment Report for Zytiga (abiraterone) published 2011 by the CHMP of the EMA.
Auchuz-3, R.J,, "The genetics, pathophysiology, and the management of human deficiencies of P450c17", Endocrinol Metab Clin North Am (2001), 30, p. 101-119.
Ayub, M., Inhibition of testicular 17a-hydroxylase and 17,20-Iyase but not 3B-hydroxysteroid dehydrogenase-isomerase or 17B-hydroxysteroid oxidoreductase by ketoconazole and other imidazole drugs, Journal of Steroid Biochemistry (1987) 28(5), p. 521-531.
Campbell-Walsh Urology, Ninth Edition, Saunders, vol. 3, Chapters 104 and 105, 2007.
Cecil Textbook of Medicine, Wyngaarden & Smith 18th edition; Chapter on "Glucocorticosteroid Therapy", Wyngaarden & Smith 18th edition, (1988) p. 128-131.
Coudar Biotechnology Inc. with the U.S. Securities and Exchange Commission, Form 10-QSB, 2013.
Czock, et al., "Pharmacokinetics and Pharmacodynamics of Systemically Administered Glucocorticoids", Pharmacokinet (2005), 44(1), p. 61-98.
Ergun-Longmire, Berrin, et al., "Two Novel Mutations Found in a Patient with 17a-Hydroxylase Enzyme Deficiency", The Journal of Clinical Endocrinology & Metabolism (2006), 91(10), p. 4179-4182.
Fakih, et al., Urology (2002) 60, p. 553-561.
Friel, Patrick N., et al., "Suppression of adrenal function by low-dose prednisone: assessment with 24-hour urinary steroid hormone profiles—A review of five cases", Alternative Medicine Review (2006), 11(1).
Internet article: http://clinicaltrials.gov/archive/NCT00485303/2007_06_11.
Information concerning Zytiga (abiraterone acetate) from http://www.kompendium.ch/prod/pnr/1183238/de?Platform=Desktop as of Mar. 25, 2014.
Internet article: http://clinicaltrials.gov/ct2/show/study/NCT00485303?sec=X501, 2014.
Mostaghel, E.A., "Abiraterone in the treatment of metastatic castration-resistant prostate cancer", Cancer Management Res. (2014) 6, p. 39-51.
Osaba, D., et al., "Health-Related Quality of Life in Men with Metastatic Prostate Cancer Treated with Prednisone alone or Mitoxantrone and Prednisone", J Clin. Oncol. (1999), 17(6), p. 165-1663.
Petrylak, D.P., "New Paradigms for Advanced Prostate Cancer", Rev. Urol. (2007), 9, Suppl. 2, S3-S12.
Prostate Cancer Principles and Practice, Taylor & Francis (2006) Chapter 93.
Reid, A., et al., "Annals of Oncology", Educational and Abstract Book of the ESMO Conference Lugano (ECLU), (2007), 18(Supplement 9), ix173-ix174. Abstract 50PD.
Remington, The Science and Practice of Pharmacy, 20th Edition (2000), p. 1363-1370.
Runge, Marschall S., et al., Principles of Molecular Medicine; Second edition; (2006) Humana Press Inc. ISBN: 1-58829-202-9. pp. 365-376 and 482-484.
Sills, Irene N., et al., "17a-hydroxylase deficiency in a genetic male and female sibling pair", Int. J. Gynaecol. Obstet., (1981), 19, p. 473-479.
Summary of Product Characteristics for Zytiga 250mg tablets (Jan. 16, 2014).
Tannock., et al., "Docetaxel Plus Prednisone or Mitoxantrone Plus Prednisone for Advanced Prostate Cancer", Journal of Urology (2005), 173(2), p. 456.
The reply of applicant (i.e. the Proprietor of herein opposed patent) dated Jun. 4, 2013 in relation to the corresponding US2011/0144016A1 US proceedings.
Wang, C., et al., "Hypertension due to 17a-Hydroxylase deficiency", Australian and New Zealand Journal of Medicine (1978), 8(3), p. 295-299.
Yano, A., et al., "Glucocorticoids Suppress Tumor Angiogensis and In vivo Growth of Prostate Cancer Cells", Clin. Cancer Res., (2006) 12, 3003-3009.
Statement of Opposition, Actavis Group PTC ehf, 2014.
Statement of Opposition, Alfred E. Tiefenbacher, 2014.
Statement of Opposition, Alison Gallafent, 2014.
Statement of Opposition, Arnold Siedsma, 2014.
Statement of Opposition, Cabinet Lavoix, 2014.
Statement of Opposition, Galenicum Health, S.L., 2014.
Statement of Opposition, Generics Ltd., 2014.
Statement of Opposition, Helm AG, 2014.
Statement of Opposition, Hetero Drugs, 2014.
Statement of Opposition, Isenbruck Bosl Horschler LLP, 2014.
Statement of Opposition, Laboratorios Leon Farma, S.A., 2014.
Statement of Opposition, Maiwald Patentanwalts GmbH, 2014.
Statement of Opposition, Stada Arzneimittel, 2014.
Statement of Opposition, Synthon B.V., 2014.

(56) References Cited

OTHER PUBLICATIONS

Statement of Opposition, Teva Pharmaceutical Industries, Ltd., 2014.
Statement of Opposition, Zentiva k.s., 2014.
Carducci, M.A., "What is more exciting? The Activity of Docetaxel in Early Prostate Cancer or the Successful Collaboration between Urologists and Medical Oncologists to complete a study in early Prostate Cancer'?", Journal of Clinical Oncology (2005), vol. 23, No. 15, pp. 3304-3307.
Sahu, B., et al,, "FoxA1 Specifies Unique Androgen and Glucocorticoid Receptor Binding Events in Prostate Cancer Cells", Cancer Research (2013), vol. 73, pp. 1570-1580.
Storlie, J.A., et al., "Prostate Specific Antigen Levels and Clinical Response to Low Dose Dexamethasone for Hormone-Refractory Metastatic Prostate Carcinoma", Cancer (1995) vol. 76, No. 1, p. 96-100.
Tanagho, E.A., et al., "The Leading Single-Volume Resource in Urology", Smith's General Urology, 16th Edition, (2004), Chapter 19, pp. 321-323; Chapter 22, pp. 380-385.
Tomic, R., et al,, "Hormonal Effects of High Dose Medroxyprogesterone Acetate Treatment in Males with Renal or Prostatic Adenocarcinoma", (1988), vol. 22 (1), Abstract.
Venkitaraman, R., et al., "Efficacy of Low-Dose Dexarnethasone in Castration-Refractory Prostate Cancer", BJU Int (2008), 101, pp. 1756-1764.
Vogelzang, N.J., Curriculum Vitae, 15 pages.
Yana, A., et al., "Glucocorticoids Suppress Tumor Lymphandiogenesis of Prostate Cancer Cells", Clin Cancer Res (2006), vol. 12, pp. 6012-6017.
Declaration by Dr. Jacqueline Anne Warner in the matter of Opposition by Northern Rivers Pty Ltd., 25 pages, 2004.
Declaration by Helen Grimes in the matter of Opposition by Northern Rivers Pty Ltd., 43 pages, 2004.
Statement of Opposition, Actavis Group PTC ehf.
Statement of Opposition, Alfred E. Tiefenbacher (translated in English).
Statement of Opposition, Arnold Siedsma (Synthon B.V.).
Statement of Opposition, Cabinet Lavoix.
Statement of Opposition, Galenicum Health, S.L.
Statement of Opposition, Generics Ltd.
Statement of Opposition, Helm AG (translated in English).
Statement of Opposition, Hetero Drugs.
Statement of Opposition, Laboratorios Leon Farma, S.A.
Statement of Opposition, Maiwald Patentanwalts GmbH.
Statement of Opposition, Stada Arzneimittel AG (translated in English).
Statement of Opposition, Teva Pharmaceutical Industries, Ltd.

* cited by examiner

METHODS AND COMPOSITIONS FOR TREATING CANCER

FIELD OF THE INVENTION

Methods and compositions for treating cancer are described herein. More particularly, the methods for treating cancer comprise administering a 17α-hydroxylase/$C_{17,20}$-lyase inhibitor, such as abiraterone acetate (i.e., 3β-acetoxy-17-(3-pyridyl) androsta-5,16-diene), in combination with at least one additional therapeutic agent, such as an anti-cancer agent or a steroid. Furthermore, disclosed are compositions comprising a 17α-hydroxylase/$C_{17,20}$-lyase inhibitor, and at least one additional therapeutic agent such as an anti-cancer agent or a steroid, e.g., a corticosteroid or, more specifically, a glucocorticoid.

BACKGROUND

The number of people diagnosed with cancer has significantly increased. Of special interest are individuals diagnosed with androgen-dependent disorders, such as prostate cancer, and estrogen-dependent disorders, such as breast cancer since such diagnoses are increasing in number at an alarming rate.

Prostate cancer is currently the most common non-skin cancer and the second leading cause of cancer-related death in men after lung cancer. The primary course of treatment for patients diagnosed with organ-confined prostate cancer is usually prostatectomy or radiotherapy. Not only are these treatments highly invasive and have undesirable side effects, such localized treatments are not effective on prostate cancer after it has metastasized. Moreover, a large percent of individuals who receive localized treatments will suffer from recurring cancer.

Additionally, breast cancer incidence in women has increased from one out of every 20 women in 1960 to one out of every eight women in 2005. Moreover, it is the most common cancer among white and African-American women. Similar to treating prostate cancer, most options for women diagnosed with breast cancer are highly invasive and have significant side-effects. Such treatments include surgery, radiation and chemotherapy.

Hormone therapy is another treatment option for individuals diagnosed with prostate or breast cancer. Hormone therapy is a form of systemic treatment for prostate or breast cancer wherein hormone ablation agents are used to suppress the production or block the effects of hormones, such as estrogen and progesterone in the body, which are believed to promote the growth of breast cancer, as well as testosterone and dihydrotestosterone, which are believed to promote the growth of prostate cancer. Moreover, hormone therapy is less invasive than surgery and does not have many of the side effects associated with chemotherapy or radiation. Hormone therapy can also be used by itself or in addition to localized therapy and has shown to be effective in individuals whose cancer has metastasized.

Even though hormone therapy is less invasive and can be used on more advanced stages of cancer, some individuals administered current hormone therapy treatments may not show a significant response or may not show any response at all to such treatments. Additionally, some patients treated with current hormone therapy treatments may also suffer from relapsing or recurring cancer. Currently, such refractory cancer patients are left with very few treatment options.

Despite the progress made in the treatment of cancer, there remains a need for more effective ways to treat cancer such as, but not limited to, prostate cancer and breast cancer. Additionally, there is a need for effective anti-cancer treatment options for patients who are not responding to current anti-cancer treatments. Also, there is a need for effective anti-cancer treatment options for patients whose cancer has recurred.

SUMMARY OF THE INVENTION

Described herein are methods for treating a cancer in which a therapeutically effective amount of a 17α-hydroxylase/$C_{17,20}$-lyase inhibitor, such as abiraterone acetate (i.e. 3β-acetoxy-17-(3-pyridyl)androsta-5,16-diene), is administered to a patient, a patient in need thereof, in combination with a therapeutically effective amount of at least one additional therapeutic agent including, but not limited to, an anti-cancer agent or steroid. Such methods can also provide an effective treatment for individuals with a refractory cancer, including individuals who are currently undergoing a cancer treatment. Therefore, in certain embodiments, the method is directed to treating a refractory cancer in a patient, in which a therapeutically effective amount of 17α-hydroxylase/$C_{17,20}$-lyase inhibitor is administered to a patient currently receiving an anti-cancer agent.

For example, in certain embodiments, the method for the treatment of a cancer in a mammal comprises administering an amount of about 0.01 mg/kg/day to about 100 mg/kg/day of abiraterone acetate and an amount of about 0.1 mg/m² to about 20 mg/m² of mitoxantrone.

In another embodiment, the method for the treatment of a cancer in a mammal comprises administering an amount of about 0.01 mg/kg/day to about 100 mg/kg/day of abiraterone acetate and an amount of about 1 mg/m² to about 175 mg/m² of paclitaxel.

In still other embodiments, the method for the treatment of a cancer in a mammal comprises administering an amount of about 0.01 mg/kg/day to about 100 mg/kg/day of abiraterone acetate and an amount of about 1 mg/m² to about 100 mg/m² of docetaxel.

Furthermore, described herein is a method for the treatment of a cancer in a mammal comprising administering an amount of about 0.01 mg/kg/day to about 100 mg/kg/day of abiraterone acetate; and an amount of about 0.01 mg to about 200 mg of leuprolide, wherein the leuprolide is administered over a period of about 3 days to about 12 months.

In other embodiments, the method for the treatment of a cancer in a mammal comprises administering an amount of about 0.01 mg/kg/day to about 100 mg/kg/day of abiraterone acetate and an amount of about 0.01 mg to about 20 mg of goserelin, wherein the goserelin is administered over a period of about 28 days to about 3 months.

Additionally, in another embodiment, the method for the treatment of a cancer in a mammal comprises administering an amount of about 0.01 mg/kg/day to about 100 mg/kg/day of abiraterone acetate and an amount of about 0.01 mg to about 20 mg of triptorelin, wherein the triptorelin is administered over a period of about 1 month.

The method for the treatment of a cancer in a mammal can also comprise administering an amount of about 0.01 mg/kg/day to about 100 mg/kg/day of abiraterone acetate and an amount of about 0.1 μg/day to about 500 μg/day of seocalcitol, such as about 100 μg/day of seocalcitol.

Also, the method for the treatment of a cancer in a mammal can comprise administering an amount of about 0.01 mg/kg/day to about 100 mg/kg/day of abiraterone acetate and an amount of about 1 mg/day to about 300 mg/day of bicalutamide.

In yet another embodiment, the method for the treatment of a cancer in a mammal can comprise administering an amount of about 0.01 mg/kg/day to about 100 mg/kg/day of abiraterone acetate and an amount of about 1 mg/day to about 2000 mg/day of flutamide.

Moreover, the method for the treatment of a cancer in a mammal can comprise administering an amount of about 50 mg/day to about 2000 mg/day of abiraterone acetate and an amount of about 0.01 mg/day to about 500 mg/day of a glucocorticoid including, but not limited to, hydrocortisone, prednisone or dexamethasone.

Also described herein are compositions for the treatment of cancer that comprise a combination of a therapeutically effective amount of at least one 17α-hydroxylase/$C_{17,20}$-lyase inhibitor and a therapeutically effective amount of at least one additional anti-cancer agent, such as, but not limited to, mitoxantrone, paclitaxel, docetaxel, leuprolide, goserelin, triptorelin, seocalcitol, bicalutamide, flutamide, or a steroid including, but not limited to, hydrocortisone, prednisone, or dexamethasone.

Finally, single unit dosage forms comprising abiraterone acetate and a glucocorticoid, optionally with carriers, diluents or excipients, are contemplated. Also, kits comprising at least one 17α-hydroxylase/$C_{17,20}$-lyase inhibitor and an additional anti cancer agent or steroid are contemplated. For example, the kit may include a vial containing abiraterone acetate and another vial containing a glucocorticoid.

DEFINITIONS

As used herein and unless otherwise defined the word "cancer," refers to the growth, division or proliferation of abnormal cells in the body. Cancers that can be treated with the methods and the compositions described herein include, but are not limited to, prostate cancer, breast cancer, adrenal cancer, leukemia, lymphoma, myeloma, Waldenström's macroglobulinemia, monoclonal gammopathy, benign monoclonal gammopathy, heavy chain disease, bone and connective tissue sarcoma, brain tumors, thyroid cancer, pancreatic cancer, pituitary cancer, eye cancer, vaginal cancer, vulvar cancer, cervical cancer, uterine cancer, ovarian cancer, esophageal cancer, stomach cancer, colon cancer, rectal cancer, liver cancer, gallbladder cancer, cholangiocarcinoma, lung cancer, testicular cancer, penal cancer, oral cancer, skin cancer, kidney cancers, Wilms' tumor and bladder cancer.

As used herein, and unless otherwise defined, the terms "treat," "treating" and "treatment" include the eradication, removal, modification, management or control of a tumor or primary, regional, or metastatic cancer cells or tissue and the minimization or delay of the spread of cancer.

As used herein, and unless otherwise defined, the term "patient" means an animal, including but not limited to an animal such as a human, monkey, cow, horse, sheep, pig, chicken, turkey, quail, cat, dog, mouse, rat, rabbit, or guinea pig. In one embodiment, the patient is a mammal and in another embodiment the patient is a human. In certain embodiments, the patient can be an adult male or female. In some embodiments, the patient is a male of age about 30 years to about 85 years. In other embodiments, the patient is a female of age about 30 years to about 85 years. In a particular embodiment, the patient has or is susceptible to having (e.g., through genetic or environmental factors) cancer. In a further embodiment, the patient has or is susceptible to having (e.g., through genetic or environmental factors) a tumor. In other embodiments, the patient can be castrated or non-castrated.

The term "17α-hydroxylase/$C_{17,20}$-lyase inhibitor" as used herein refers to an inhibitor of 17α-hydroxylase/$C_{17,20}$-lyase, (which is an enzyme in testosterone synthesis), an analog thereof, derivative thereof, metabolite thereof or pharmaceutically acceptable salt thereof. Also, unless otherwise noted, reference to a particular 17α-hydroxylase/$C_{17,20}$-lyase inhibitor can include analogs, derivatives, metabolites or pharmaceutically acceptable salts of such particular 17α-hydroxylase/$C_{17,20}$-lyase inhibitor.

The term "anti-cancer agent" as used herein refers to any therapeutic agent that directly or indirectly kills cancer cells or directly or indirectly prohibits stops or reduces the proliferation of cancer cells. It should be noted that even though throughout this specification and in the claims the phrase "anti-cancer agent" is written as a singular noun, for example; "an anti-cancer agent" or "the anti-cancer agent," the phrase "anti-cancer agent" should not be interpreted as being limited to the inclusion of a single anti-cancer agent.

As used herein, and unless otherwise defined, the phrase "therapeutically effective amount" when used in connection with a 17α-hydroxylase/$C_{17,20}$-lyase inhibitor or therapeutic agent means an amount of the 17α-hydroxylase/$C_{17,20}$-lyase inhibitor or therapeutic agent effective for treating a disease or disorder disclosed herein, such as cancer.

As used herein and unless otherwise defined the phrase "refractory cancer," means cancer that is not responding to an anti-cancer treatment or cancer that is not responding sufficiently to an anti-cancer treatment. Refractory cancer can also include recurring or relapsing cancer.

As used herein and unless otherwise defined the phrase "refractory patient," means a patient who has refractory cancer.

As used herein and unless otherwise defined the phrase "relapse cancer," means cancer that was at one time responsive to an anti-cancer treatment but has become no longer responsive to such treatment or is no longer responding sufficiently to such treatment.

As used herein and unless otherwise defined the phrase "recurring cancer," means cancer that has returned after a patient has been earlier diagnosed with cancer, under gone treatment or had been previously diagnosed as cancer-free.

As used herein and unless otherwise defined the term "derivative" refers to a chemically modified compound wherein the chemical modification takes place at one or more functional groups of the compound. The derivative may retain or improve the pharmacological activity of the compound from which it is derived.

As used herein and unless otherwise defined the term "analog" refers to a chemical compound that is structurally similar to another but differs slightly in composition (as in the replacement of one atom by an atom of a different element or in the presence of a particular functional group).

As used herein and unless otherwise defined the phrase "pharmaceutically acceptable salt" refers to any salt of a 17α-hydroxylase/$C_{17,20}$-lyase inhibitor which retains the biological effectiveness of the 17α-hydroxylase/$C_{17,20}$-lyase inhibitor. Examples of pharmaceutically acceptable salts include, but are not limited to, acetates, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phylacetates, phenylpropionates, phenylbutyrates, citrates, lactates, gamma-hydroxybutyrates, glycollates, tartarates, alkanesulfonates (e.g. methane-sulfonate or mesylate), propanesulfonates, naphthalene-1-sulfonates, naphthalene-2-sulfonates, and mandelates. Several of the officially approved salts are listed in Remington: The Science and Practice of Pharmacy, Mack Publ. Co., Easton.

DETAILED DESCRIPTION OF THE INVENTION

The methods described herein for treating cancer comprise administering to a mammal, preferably a human, a 17α-hydroxylase/$C_{17,20}$-lyase inhibitor in addition to at least one therapeutic agent, such as an anti-cancer agent or steroid, particularly a glucocorticoid. The compositions described herein comprise a 17α-hydroxylase/$C_{17,20}$-lyase inhibitor and at least one additional therapeutic agent, such as an anti-cancer agent or steroid, particularly a corticosteroid or glucocorticoid. Other anti-cancer treatments such as, administration of yet another anti-cancer agent, radiotherapy, chemotherapy, photodynamic therapy, surgery or other immunotherapy, can be used with the methods and compositions.

17α-Hydroxylase/$C_{17,20}$-Lyase Inhibitors

17α-hydroxylase/$C_{17,20}$-lyase inhibitors have been shown to be useful in the treatment of cancer, specifically hormone-dependent disorders such as, androgen-dependent and estrogen-dependent disorders like prostate cancer and breast cancer respectively, as described in U.S. Pat. No. 5,604,213 to Barrie et al., which is herein incorporated by reference in its entirety.

In certain embodiments, the 17α-hydroxylase/$C_{17,20}$-lyase inhibitor can be 17-(3-pyridyl)androsta-5,16-dien-3βol; 17-(3-pyridyl)androsta-3,5,16-triene; 17-(3-pyridyl)androsta-4,16-dien-3-one; 17-(3-pyridyl)estra-1,3,5[10],16-tetraen-3-ol; 17-(3-pyridyl)-5α-androst-16-en-3α-ol; 17-(3-pyridyl)-5α-androst-16-en-3-one; 17-(3-pyridyl)-androsta-4,16-diene-3,11-dione; 17-(3-pyridyl)-androsta-3,5,16-trien-3-ol; 6α- and 6β-fluoro-17-(3-pyridyl)androsta-4,16-dien-3-one; 17-(3-pyridyl)androsta-4,16-dien-3,6-dione; 3α-trifluoromethyl-17-(3-pyridyl)androst-16-en-3β-ol or their acid addition salts and 3-esters as well as metabolites, analogs, derivatives or a pharmaceutically acceptable salt thereof.

In certain embodiments, the 17α-hydroxylase/$C_{17,20}$-lyase inhibitor can have the structure of formula (I):

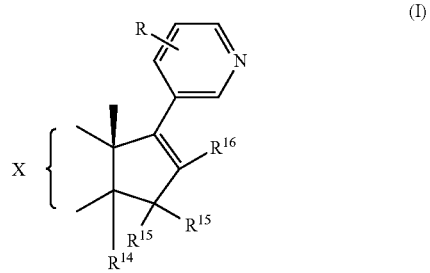

(I)

wherein X represents the residue of the A, B and C rings of a steroid which can be, without limitation, androstan-3α- or 3β-ol; androst-5-en-3β- or 3β-ol; androst-4-en-3-one; androst-2-ene; androst-4-ene; androst-5-ene; androsta-5,7-dien-3α or 3β-ol; androsta-1,4-dien-3-one; androsta-3,5-diene; androsta-3,5-diene-3-ol; estra-1,3,5[10]-triene; estra-1,3,5[10]-trien-3-ol; 5α-androstan-3-one; androst-4-ene-3,11-dione; 6-fluoroandrost-4-ene-3-one; or androstan-4-ene-3,6-dione; each of which, where structurally permissible, can be further derivatized in one or more of the following ways, including, but not limited to, to form 3-esters; to have one or more carbon or carbon ring double bonds in any of the 5,6-, 6,7-, 7,8-, 9,11- and 11,12-positions; as 3-oximes; as 3-methylenes; as 3-carboxylates; as 3-nitriles; as 3-nitros; as 3-desoxy derivatives; to have one or more hydroxy, halo, $C_{1-4}$-alkyl, trifluoro-methyl, $C_{1-4}$-alkoxy, $C_{1-4}$-alkanoyloxy, benzoyloxy, oxo, methylene or alkenyl substituents in the A, B, or C-ring; or to be 19-nor;

R represents a hydrogen atom or an alkyl group of 1-4 carbon atoms;

$R^{14}$ represents a hydrogen atom, a halogen atom or an alkyl group of 1 to 4 carbon atoms;

each of the $R^{15}$ substituents independently represents a hydrogen atom or an alkyl or alkoxy group of 1-4 carbon atoms, a hydroxy group or an alkylcarbonyloxy group of 2 to 5 carbon atoms or together represent an oxo or methylene group or $R^{14}$ and one of the $R^{15}$ groups together represent a double bond and the other $R^{15}$ group represents a hydrogen atom or an alkyl group of 1 to 4 carbon atoms; and $R^{16}$ represents a hydrogen atom, halogen atom, or an alkyl group of 1 to 4 carbon atoms, in the form of the free bases or pharmaceutically acceptable acid addition salts, but excluding 3β-acetoxy-17-(3-pyridyl)androsta-5,14,16-triene, 3β,15α- and 3β,15β-diacetoxy-17-(3-pyridyl)androsta-5,16-diene and 3β-methoxy-17-(3-pyridyl-5α-androst-16-ene.

Suitable inhibitors also include metabolites, derivatives, analogs, or pharmaceutically acceptable salts of formula (I).

In another embodiment, the 17α-hydroxylase/$C_{17,20}$-lyase inhibitor can have the structure of formula (I):

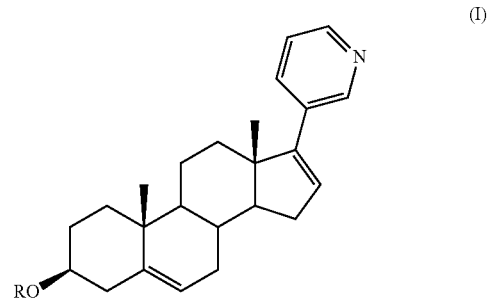

(I)

wherein R represents hydrogen or a lower acyl group having 1 to 4 carbons. Suitable inhibitors also include derivatives, analogs, or pharmaceutically acceptable salts of formula (I).

In still another embodiment, the 17α-hydroxylase/$C_{17,20}$-lyase inhibitor can be a 3β-alkanoyloxy-17-(3-pyridyl)androsta-5,16-diene in which the alkanoyloxy group has from 2 to 4 carbon atoms.

In a preferred embodiment, the 17α-hydroxylase/$C_{17,20}$-lyase inhibitor comprises abiraterone acetate or 3β-acetoxy-17-(3-pyridyl)androsta-5,16-diene which has the following structural formula:

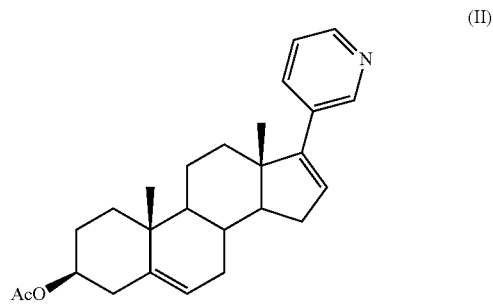 [SMILES: CC(=O)O[C@H]1CC[C@@]2(C)C(=CCC3C2CC[C@]2(C)C(c4cccnc4)=CCC32)C1]

(II)

and pharmaceutically acceptable salts thereof.

Preferred salts of abiraterone acetate and methods of making such salts are also disclosed in U.S. Provisional Application No. 60/603,559 to Hunt, which is incorporated by reference in its entirety. Preferred salts include, but are not limited to, acetates, citrates, lactates, alkanesulfonates (e.g. methanesulfonate or mesylate) and tartarates. Of special interest is the abiraterone acetate mesylate salt (i.e. 3β-acetoxy-17-(3-pyridyl)androsta-5,16-diene mesylate salt) which has the following structural formula:

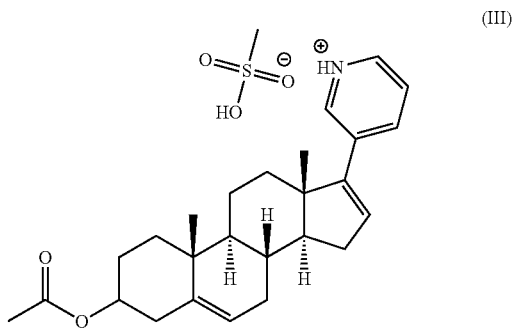

(III)

The 17α-hydroxylase/$C_{17,20}$-lyase inhibitors can be made according to any method known to one skilled in the art. For example, such inhibitors can be synthesized according to the method disclosed in U.S. Pat. Nos. 5,604,213 and 5,618,807 to Barrie et al., herein incorporated by reference. Another method of making 17α-hydroxlase/$C_{17,20}$-lyase inhibitors is disclosed in U.S. provisional application 60/603,558 to Bury, herein incorporated by reference.

The amount of 17α-hydroxylase/$C_{17,20}$-lyase inhibitor administered to a mammal having cancer is an amount that is sufficient to treat the cancer, whether the 17α-hydroxylase/$C_{17,20}$-lyase inhibitor is administered alone or in combination with an additional anti-cancer treatment, such as an additional anti-cancer agent.

Additional Therapeutic Agents

Suitable compounds that can be used in addition to 17α-hydroxylase/$C_{17,20}$-lyase inhibitors as an anti-cancer agent include, but are not limited to, hormone ablation agents, anti-androgen agents, differentiating agents, anti-neoplastic agents, kinase inhibitors, anti-metabolite agents, alkylating agents, antibiotic agents, immunological agents, interferon-type agents, intercalating agents, growth factor inhibitors, cell cycle inhibitors, enzymes, topoisomerase inhibitors, biological response modifiers, mitotic inhibitors, matrix metalloprotease inhibitors, genetic therapeutics, and anti-androgens. The amount of the additional anti-cancer agent administered to a mammal having cancer is an amount that is sufficient to treat the cancer whether administered alone or in combination with a 17α-hydroxylase/$C_{17,20}$-lyase inhibitor. Below are lists of examples of some of the above classes of anti-cancer agents. The examples are not all inclusive and are for purposes of illustration and not for purposes of limitation. Many of the examples below could be listed in multiple classes of anti-cancer agents and are not restricted in any way to the class in which they are listed in.

Suitable hormonal ablation agents include, but are not limited to, androgen ablation agents and estrogen ablation agents. In preferred embodiments, the 17α-hydroxylase/$C_{17,20}$-lyase inhibitor is administered with a hormonal ablation agent, such as deslorelin, leuprolide, goserelin or triptorelin. Even though throughout this specification and in the claims the phrase "hormonal ablation agent" is written as a singular noun, for example; "a hormonal ablation agent" or "the hormonal ablation agent," the phrase "hormonal ablation agent" should not be interpreted as being limited to the inclusion of a single hormonal ablation agent. The amount of the hormonal ablation agent administered to a mammal having cancer is an amount that is sufficient to treat the cancer whether administered alone or in combination with a 17α-hydroxylase/$C_{17,20}$-lyase inhibitor.

Suitable anti-androgen agents include but are not limited to bicalutamide, flutamide and nilutamide. The amount of the anti-androgen agent administered to a mammal having cancer is an amount that is sufficient to treat the cancer whether administered alone or in combination with a 17α-hydroxylase/$C_{17,20}$-lyase inhibitor.

In another embodiment, the 17α-hydroxylase/$C_{17,20}$-lyase inhibitor may be administered with a differentiating agent. Suitable differentiating agents include, but are not limited to, polyamine inhibitors; vitamin D and its analogs, such as, calcitriol, doxercalciferol and seocalcitol; metabolites of vitamin A, such as, ATRA, retinoic acid, retinoids; short-chain fatty acids; phenylbutyrate; and nonsteroidal anti-inflammatory agents. The amount of the differentiating agent administered to a mammal having cancer is an amount that is sufficient to treat the cancer whether administered alone or in combination with a 17α-hydroxylase/$C_{17,20}$-lyase inhibitor.

In another preferred embodiment, the 17α-hydroxylase/$C_{17,20}$-lyase inhibitor may be administered with an anti-neoplastic agent, including, but not limited to, tubulin interacting agents, topoisomerase inhibitors and agents, acitretin, alstonine, amonafide, amphethinile, amsacrine, ankinomycin, anti-neoplaston, aphidicolin glycinate, asparaginase, baccharin, batracylin, benfluron, benzotript, bromofosfamide, caracemide, carmethizole hydrochloride, chlorsulfaquinoxalone, clanfenur, claviridenone, crisnatol, curaderm, cytarabine, cytocytin, dacarbazine, datelliptinium, dihaematoporphirin ether, dihydrolenperone, dinaline, distamycin, docetaxel, elliprabin, elliptinium acetate, epothilones, ergotamine, etoposide, etretinate, fenretinide, gallium nitrate, genkwadaphnin, hexadecylphosphocholine, homoharringtonine, hydroxyurea, ilmofosine, isoglutamine, isotretinoin, leukoregulin, lonidamine, merbarone, merocyanlne derivatives, methylanilinoacridine, minactivin, mitonafide, mitoquidone, mitoxantrone, mopidamol, motretinide, N-(retinoyl)amino acids, N-acylated-dehydroalanines, nafazatrom, nocodazole derivative, ocreotide, oquizanocinc, paclitaxel, pancratistatin, pazelliptine, piroxantrone, polyhaematoporphyrin, polypreic acid, probimane, procarbazine, proglumide, razoxane, retelliptine, spatol, spirocyclopropane derivatives, spirogermanium, strypoldinone, superoxide dismutase, teniposide, thaliblastine, tocotrienol, topotecan, ukrain, vinblastine sulfate, vincristine, vindesine, vinestramide, vinorelbine, vintriptol, vinzolidine, and withanolides. The amount of the anti-neoplastic agent administered to a mammal having cancer is an amount that is sufficient to treat the cancer whether administered alone or in combination with a 17α-hydroxylase/$C_{17,20}$-lyase inhibitor.

The 17α-hydroxylase/$C_{17,20}$-lyase inhibitors may also be used with a kinase inhibitor including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, SOD mimics or $\alpha_v\beta_3$ inhibitors. The amount of the kinase inhibitor administered to a mammal having cancer is an amount that is sufficient to treat the cancer whether administered alone or in combination with a 17α-hydroxylase/$C_{17,20}$-lyase inhibitor.

In another embodiment, the 17α-hydroxylase/$C_{17,20}$-lyase inhibitor may be administered with an anti-metabolite agent.

Suitable anti-metabolite agents may be selected from, but not limited to, 5-FU-fibrinogen, acanthifolic acid, aminothiadiazole, brequinar sodium, carmofur, cyclopentyl cytosine, cytarabine phosphate stearate, cytarabine conjugates, dezaguanine, dideoxycytidine, dideoxyguanosine, didox, doxifluridine, fazarabine, floxuridine, fludarabine phosphate, 5-fluorouracil, N-(2'-furanidyl)-5-fluorouracil, isopropyl pyrrolizine, methobenzaprim, methotrexate, norspermidine, pentostatin, piritrexim, plicamycin, thioguanine, tiazofurin, trimetrexate, tyrosine kinase inhibitors, and uricytin. The amount of the anti-metabolite agent administered to a mammal having cancer is an amount that is sufficient to treat the cancer whether administered alone or in combination with a 17α-hydroxylase/$C_{17,20}$-lyase inhibitor.

In another embodiment, the 17α-hydroxylase/$C_{17,20}$-lyase inhibitor may be administered with an alkylating agent. Suitable alkylating agents may be selected from, but not limited to, aldo-phosphamide analogues, altretamine, anaxirone, bestrabucil, budotitane, carboplatin, carmustine, chlorambucil, cisplatin, cyclophosphamide, cyplatate, diphenylspiromustine, diplatinum cytostatic, elmustine, estramustine phosphate sodium, fotemustine, hepsul-fam, ifosfamide, iproplatin, lomustine, mafosfamide, mitolactol, oxaliplatin, prednimustine, ranimustine, semustine, spiromustine, tauromustine, temozolomide, teroxirone, tetraplatin and trimelamol. The amount of the alkylating agent administered to a mammal having cancer is an amount that is sufficient to treat the cancer whether administered alone or in combination with a 17α-hydroxylase/$C_{17,20}$-lyase inhibitor.

In another preferred embodiment, the 17α-hydroxylase/$C_{17,20}$-lyase inhibitor may be administered with an antibiotic agent. Suitable antibiotic agents may be selected from, but not limited to, aclarubicin, actinomycin D, actinoplanone, adriamycin, aeroplysinin derivative, amrubicin, anthracycline, azino-mycin-A, bisucaberin, bleomycin sulfate, bryostatin-1, calichemycin, chromoximycin, dactinomycin, daunorubicin, ditrisarubicin B, dexamethasone, doxorubicin, doxorubicin-fibrinogen, elsamicin-A, epirubicin, erbstatin, esorubicin, esperamicin-A1, esperamicin-A1b, fostriecin, glidobactin, gregatin-A, grincamycin, herbimycin, corticosteroids such as hydrocortisone, idarubicin, illudins, kazusamycin, kesarirhodins, menogaril, mitomycin, neoenactin, oxalysine, oxaunomycin, peplomycin, pilatin, pirarubicin, porothramycin, prednisone, prednisolone, pyrindanycin A, rapamycin, rhizoxin, rodorubicin, sibanomicin, siwenmycin, sorangicin-A, sparsomycin, talisomycin, terpentecin, thrazine, tricrozarin A, and zorubicin. The amount of the antibiotic agent administered to a mammal having cancer is an amount that is sufficient to treat the cancer whether administered alone or in combination with a 17α-hydroxylase/$C_{17,20}$-lyase inhibitor.

Alternatively, the 17α-hydroxylase/$C_{17,20}$-lyase inhibitors may also be used with other anti-cancer agents, including but not limited to, acemannan, aclarubicin, aldesleukin, alemtuzumab, alitretinoin, altretamine, amifostine, amsacrine, anagrelide, anastrozole, ancestim, bexarotene, broxuridine, capecitabine, celmoleukin, cetrorelix, cladribine, clotrimazole, daclizumab, dexrazoxane, dilazep, docosanol, doxifluridine, bromocriptine, carmustine, cytarabine, diclofenac, edelfosine, edrecolomab, eflornithine, emitefur, exemestane, exisulind, fadrozole, filgrastim, finasteride, fludarabine phosphate, formestane, fotemustine, gallium nitrate, gemcitabine, glycopine, heptaplatin, ibandronic acid, imiquimod, iobenguane, irinotecan, irsogladine, lanreotide, leflunomide, lenograstim, lentinan sulfate, letrozole, liarozole, lobaplatin, lonidamine, masoprocol, melarsoprol, metoclopramide, mifepristone, miltefosine, mirimostim, mitoguazone, mitolactol, molgramostim, nafarelin, nartograstim, nedaplatin, nilutamide, noscapine, oprelvekin, osaterone, oxaliplatin, pamidronic acid, pegaspargase, pentosan polysulfate sodium, pentostatin, picibanil, pirarubicin, porfimer sodium, raloxifene, raltitrexed, rasburicase, rituximab, romurtide, sargramostim, sizofiran, sobuzoxane, sonermin, suramin, tasonermin, tazarotene, tegafur, temoporfin, temozolomide, teniposide, tetrachlorodecaoxide, thalidomide, thymalfasin, thyrotropin alfa, topotecan, toremifene, trastuzumab, treosulfan, tretinoin, trilostane, trimetrexate, ubenimex, valrubicin, verteporfin, vinorelbine. The amount of the anti-cancer agent administered to a mammal having cancer is an amount that is sufficient to treat the cancer whether administered alone or in combination with a 17α-hydroxylase/$C_{17,20}$-lyase inhibitor.

The 17α-hydroxylase/$C_{17,20}$-lyase inhibitors may also be administered or combined with steroids, such as corticosteroids or glucocorticoids. The 17α-hydroxylase/$C_{17,20}$-lyase inhibitors and the steroid may be administered in the same or in different compositions. Non-limiting examples of suitable steroids include hydrocortisone, prednisone, or dexamethasone. The amount of the steroid administered to a mammal having cancer is an amount that is sufficient to treat the cancer whether administered alone or in combination with a 17α-hydroxylase/$C_{17,20}$-lyase inhibitor.

In one embodiment, provided herein are methods and compositions comprising both abiraterone acetate and a steroid particularly a corticosteroid, or more particularly a glucocorticoid. Steroids within the scope of the disclosure include, but are not limited to, (1) hydrocortisone (cortisol; cyprionate (e.g., CORTEF), oral; sodium phosphate injection (HYDROCORTONE PHOSPHATE); sodium succinate (e.g., A-HYDROCORT, Solu-CORTEF); cortisone acetate oral or injection forms, etc.), (2) dexamethasone (e.g., Decadron, oral; Decadron-LA injection, etc.), (3) prednisolone (e.g., Delta-CORTEF, prednisolone acetate (ECONOPRED), prednisolone sodium phosphate (HYDELTRASOL), prednisolone tebutate (HYDELTRA-TBA, etc.)), or (4) prednisone DELTASONE, etc.) and combinations thereof. See, e.g., GOODMAN & GILMAN'S THE PHARMACOLOGICAL BASIS OF THERAPEUTICS, $10^{TH}$ EDITION 2001.

In a specific embodiment, single unit solid oral dosage forms which comprise an amount from about 50 mg to about 300 mg of abiraterone acetate and an amount from about 0.5 mg to about 3.0 mg of a steroid, e.g., glucocorticoid in a single composition, optionally with excipients, carriers, diluents, etc. is contemplated. For instance, the single unit dosage form can comprise about 250 mg of abiraterone acetate and about 1.0 mg, 1.25 mg, 1.5 mg, or 2.0 mg of a steroid, such as but not limited to corticosteroids or glucocorticoids.

Administration of the 17α-Hydroxylase/$C_{17,20}$-Lyase Inhibitor and an Additional Therapeutic Agent The 17α-hydroxylase/$C_{17,20}$-lyase inhibitor and the additional therapeutic agent, such as an anti-cancer agent or a steroid can be administered by any method known to one skilled in the art. In certain embodiments, the 17α-hydroxylase/$C_{17,20}$-lyase inhibitor and the additional therapeutic agent can be in separate compositions prior to administration. In the alternative, the 17α-hydroxylase/$C_{17,20}$-lyase inhibitor and the additional therapeutic agent can be combined into a single composition for administration.

The 17α-hydroxylase/$C_{17,20}$-lyase inhibitor and the additional therapeutic agent can be administered sequentially or simultaneously. If administered sequentially, the order of administration is flexible. For instance, 17α-hydroxylase/$C_{17,20}$-lyase inhibitor acetate can be administered prior to administration of the additional therapeutic agent. Alternatively, administration of the additional therapeutic agent can precede administration of 17α-hydroxylase/$C_{17,20}$-lyase inhibitor.

Whether they are administered as separate compositions or in one composition, each composition is preferably pharmaceutically suitable for administration. Moreover, the 17α-hydroxylase/$C_{17,20}$-lyase inhibitor and the therapeutic agent, if administered separately, can be administered by the same or different modes of administration. Examples of modes of administration include parenteral (e.g., subcutaneous, intramuscular, intraorbital, intracapsular, intraspinal, intrasternal, intravenous, intradetinal, intraperitoneal, intraportal, intra-arterial, intrathecal, transmucosal, intra-articular, and intrapleural), transdermal (e.g., topical), epidural, and mucosal (e.g., intranasal) injection or infusion, as well as oral, inhalation, pulmonary, and rectal administration. In specific embodiments, both are oral.

For example, the 17α-hydroxylase/$C_{17,20}$-lyase inhibitor can be administered transdermally and the additional therapeutic agent can be administered parenterally. Alternatively, the 17α-hydroxylase/$C_{17,20}$-lyase inhibitor can be administered orally, such as in a tablet, caplet or capsule, while the additional therapeutic agent can be administered intravenously. Such intravenous administered therapeutic agents include, but are not limited to, docetaxel injections, such as Taxotere®; paclitaxel injections, such as Paclitaxel® and mitoxantrone injections, such as Novantrone®. Also, the additional therapeutic agent can be in the form of depots or implants such as leuprolide depots and implants, e.g. Viadur® and Lupron Depot®; triptorelin depots, e.g. Trelstar®; goserelin implants, e.g. Zoladex®.

The suitable daily dosage of the 17α-hydroxylase/$C_{17,20}$-lyase inhibitor depends upon a number of factors, including, the nature of the severity of the condition to be treated, the particular inhibitor, the route of administration and the age, weight, and response of the individual patient. Suitable daily dosages of 17α-hydroxylase/$C_{17,20}$-lyase inhibitors can generally range from about 0.0001 mg/kg/day to about 1000 mg/kg/day, or from about 0.001 mg/kg/day to about 200 mg/kg/day, or from about 0.01 mg/kg/day to about 200 mg/kg/day, or from about 0.01 mg/kg/day to about 100 mg/kg/day in single or multiple doses.

In some embodiments, the 17α-hydroxylase/$C_{17,20}$-lyase inhibitor can be administered in an amount from about 0.004 mg/day to about 5,000 mg/day, or from about 0.04 mg/day to about 3,000 mg/day, or from about 0.4 mg/day to about 1500 mg/day. In certain embodiments, the 17α-hydroxylase/$C_{17,20}$-lyase inhibitor can be administered in an amount from about 0.1 mg/day to about 2000 mg/day or from about 1 mg/day to about 2000 mg/day or from about 50 mg/day to about 2000 mg/day or from about 100 mg/day to about 1500 mg/day or from about 5 mg/day to about 1,000 mg/day or from about 5 mg/day to about 900 mg/day or from about 10 mg/day to about 800 mg/day or from about 15 mg/day to about 700 mg/day or from about 20 mg/day to about 600 mg/day or from about 25 mg/day to about 500 mg/day in single or multiple doses.

In certain embodiments, the 17α-hydroxylase/$C_{17,20}$-lyase inhibitor is co-administered with an additional anti-cancer agent such as mitoxantrone, paclitaxel or docetaxel. For example, a method for the treatment of a cancer in a mammal comprises administering an amount of abiraterone acetate and an amount of mitoxantrone. For example, the abiraterone acetate can be administered in an amount of about 0.01 mg/kg/day to about 100 mg/kg/day and the mitoxantrone can be administered in an amount of about 0.1 mg/m$^2$ to about 20 mg/m$^2$. Preferably, the mitoxantrone is administered over a period of between about 10 to about 20 minutes once every 21 days.

Also, a method for the treatment of a cancer in a mammal can comprise administering an amount of abiraterone acetate and an amount of paclitaxel. In one embodiment, the abiraterone acetate can be administered in an amount of about 0.01 mg/kg/day to about 100 mg/kg/day and the paclitaxel can be administered in the amount of about 1 mg/m$^2$ to about 175 mg/m$^2$. Preferably, the paclitaxel is administered over a period of between about 2 to about 5 hours once every three months.

Additionally, a method for the treatment of a cancer in a mammal comprises administering an amount of abiraterone acetate and an amount of docetaxel. For example, the abiraterone acetate can be administered in an amount of about 0.01 mg/kg/day to about 100 mg/kg/day and the docetaxel can be administered in an amount of about 1 mg/m$^2$ to about 100 mg/m$^2$. Preferably, the docetaxel is administered over a period of between about 1 to about 2 hours once every three weeks.

In certain embodiments, the 17α-hydroxylase/$C_{17,20}$-lyase inhibitor is administered along with an anti-cancer agent that comprises a hormonal ablation agent, including, but not limited to, leuprolide, goserelin, or triptorelin. For example, one method for the treatment of a cancer in a mammal also comprises administering an amount of abiraterone acetate and an amount of leuprolide. The amount of abiraterone acetate can be about 0.01 mg/kg/day to about 100 mg/kg/day and the amount of leuprolide can be about 0.01 mg to about 200 mg over a period of about 3 days to about 12 months. Preferably, the leuprolide is administered in the amount of about 3.6 mg of leuprolide over a period of about 3 days to about 12 months.

Additionally, the methods for the treatment of cancer in a mammal include administering an amount of abiraterone acetate and an amount of goserelin. For example, the amount of abiraterone acetate can be about 0.01 mg/kg/day to about 100 mg/kg/day and the amount of goserelin can be about 0.01 mg to about 20 mg over a period of about 28 days to about 3 months. Preferably, the goserelin is administered in the amount of about 3.6 mg to about 10.8 mg over a period of about 28 days to about 3 months.

In certain embodiments the methods for the treatment of cancer in a mammal comprises administering an amount of abiraterone acetate and an amount of triptorelin. For example, the amount of abiraterone acetate can be about 0.01 mg/kg/day to about 100 mg/kg/day and the amount of triptorelin can be about 0.01 mg to about 20 mg, over a period of about 1 month, preferably the triptorelin is administered in the amount of about 3.75 mg over a period of about 1 month.

Also, in one embodiment, the method for the treatment of a cancer in a mammal comprises administering an amount of abiraterone acetate and an amount of seocalcitol. For instance, the method involves administering an amount of about 0.01 mg/kg/day to about 100 mg/kg/day of abiraterone acetate and an amount of about 0.1 µg/day to about 500 µg/day of seocalcitol, such as about 100 µg/day of seocalcitol.

In another embodiment, the method for the treatment of a cancer in a mammal comprises administering an amount of abiraterone acetate and an amount of bicalutamide. For instance, the method involves administering an amount of about 0.01 mg/kg/day to about 100 mg/kg/day of abiraterone acetate and an amount of about 1 mg/day to about 300 mg/day of bicalutamide.

In yet another embodiment, the method for the treatment of a cancer in a mammal comprises administering an amount of abiraterone acetate and an amount of flutamide. For example, the method comprises administering an amount of about 0.01 mg/kg/day to about 100 mg/kg/day of abiraterone acetate and an amount of about 1 mg/day to about 2000 mg/day of flutamide.

Moreover, the method for the treatment of a cancer in a mammal can comprise administering an amount of a 17α-hydroxylase/$C_{17,20}$-lyase inhibitor such as abiraterone acetate and an amount of a glucocorticoid including, but not limited to, hydrocortisone, prednisone or dexamethasone. For example, the method can comprise administering an amount of about 50 mg/day to about 2000 mg/day of abiraterone acetate and an amount of about 0.01 mg/day to about 500 mg/day of hydrocortisone. In other instances, the method can comprise administering an amount of about 500 mg/day to about 1500 mg/day of abiraterone acetate and an amount of about 10 mg/day to about 250 mg/day of hydrocortisone.

The method for the treatment of a cancer can also comprise administering an amount of a 17α-hydroxylase/$C_{17,20}$-lyase inhibitor, such as abiraterone acetate, and an amount of a glucocorticoid, such as prednisone. For example, the method can comprise administering an amount of about 50 mg/day to about 2000 mg/day of abiraterone acetate and an amount of about 0.01 mg/day to about 500 mg/day of prednisone. Also, the method can comprise administering an amount of about 500 mg/day to about 1500 mg/day of abiraterone acetate and an amount of about 10 mg/day to about 250 mg/day of prednisone.

In addition, the method for the treatment of a cancer can also comprise administering an amount of a 17α-hydroxylase/$C_{17,20}$-lyase inhibitor, such as abiraterone acetate, and an amount of a glucocorticoid, such as dexamethasone. For example, the method can comprise administering an amount of about 50 mg/day to about 2000 mg/day of abiraterone acetate and an amount of about 0.01 mg/day to about 500 mg/day of dexamethasone. Also, the method can comprise administering an amount of about 500 mg/day to about 1500 mg/day of abiraterone acetate and an amount of about 0.5 mg/day to about 25 mg/day of dexamethasone.

Compositions Containing a 17α-Hydroxylase/$C_{17,20}$-Lyase Inhibitor and an Additional Therapeutic Agent In certain embodiments, the compositions can contain a combination of a 17α-hydroxylase/$C_{17,20}$-lyase inhibitor, preferably abiraterone acetate, and any of the therapeutic agents recited above. Whether the 17α-hydroxylase/$C_{17,20}$-lyase inhibitor and the additional therapeutic agent are administered in separate compositions or as a single composition, the compositions can take various forms. For example, the compositions can take the form of solutions, suspensions, emulsions, tablets, pills, capsules, powders or sustained-release formulations, depending on the intended route of administration.

For topical or transdermal administration, the compositions can be formulated as solutions, gels, ointments, creams, suspensions or salves.

For oral administration, the compositions may be formulated as tablets, pills, dragees, troches, capsules, liquids, gels, syrups, slurries, suspensions and the like, for oral ingestion by a patient to be treated.

The composition may also be formulated in rectal or vaginal compositions such as suppositories or retention enemas that contain conventional suppository bases such as cocoa butter or other glycerides.

In addition to the formulations described previously, the composition may also be formulated as a depot preparation. Such long acting formulations may be administered by implantation (for example subcutaneously or intramuscularly) or by intramuscular injection. Thus, for example, the therapeutic agents may be formulated with suitable polymeric or hydrophobic materials (for example as an emulsion in an acceptable oil) or ion exchange resins, or as sparingly soluble derivatives, for example, as a sparingly soluble salt.

Additionally, the composition may be delivered using a sustained-release system, such as semi-permeable matrices of solid polymers containing the composition. Various forms of sustained-release materials have been established and are well known by those skilled in the art. Sustained-release capsules may, depending on their chemical nature can release the composition over a period of hours, days, weeks, months. For example a sustained release capsule can release the compositions over a period of 100 days or longer. Depending on the chemical nature and the biological stability of the composition, additional strategies for stabilization may be employed.

The compositions can further comprise a pharmaceutically acceptable carrier. The term "carrier" refers to a diluent, adjuvant (e.g., Freund's adjuvant (complete and incomplete)), excipient, or vehicle with which the therapeutic is administered.

For parenteral administrations, the composition can comprise one or more of the following carriers: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium hi sulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For oral solid formulations suitable carriers include fillers such as sugars, e.g., lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, fats and oils; granulating agents; and binding agents such as microcrystalline cellulose, gum tragacanth or gelatin; disintegrating agents, such as cross-linked polyvinylpyrrolidone, agar, or alginic acid or a salt thereof such as sodium alginate, Primogel, or corn starch; lubricants, such as magnesium stearate or Sterotes; glidants, such as colloidal silicon dioxide; a sweetening agent, such as sucrose or saccharin; or flavoring agents, such as peppermint, methyl salicylate, or orange flavoring. If desired, solid dosage forms may be sugar-coated or enteric-coated using standard techniques.

For intravenous administration, suitable carriers include physiological saline, bacteriostatic water, phosphate buffered saline (PBS). In all cases, the composition must be sterile and should be fluid to the extent that easy injectability with a syringe. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars; polyalcohols such as mannitol, sorbitol; sodium chloride in the composition. Prolonged absorption of the injectable compositions can be brought about by including in the composition an agent which delays absorption, for example, aluminum monostearate and gelatin.

Also for intravenous administration, the compositions may be formulated in solutions, preferably in physiologically compatible buffers such as Hanks's solution, Ringer's solution, or physiological saline buffer. The solution may contain formulatory agents such as suspending, stabilizing and/or dispersing agents. In a preferred embodiment, the compositions are formulated in sterile solutions.

For transmucosal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories.

For administration by inhalation, the compositions may be formulated as an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator may be formulated containing a powder mix of the composition and a suitable powder base such as lactose or starch.

The pharmaceutical compositions may be manufactured by means of conventional mixing, dissolving, granulating, dragee-making, levigating, emulsifying, encapsulating, entrapping or lyophilizing processes.

One example of a composition comprising a 17α-hydroxylase/$C_{17,20}$-lyase inhibitor and an additional therapeutic agent is an oral composition or composition suitable for oral administration comprising abiraterone acetate in combination with a steroid. For example, the oral composition can be a solid dosage form such as a pill, a tablet or a capsule. The oral composition can comprise about 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg of abiraterone acetate. The oral composition can comprises about 0.25 mg, 0.5 mg, 0.75 mg, 1.0 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5.0 mg, 7.5 mg, 10 mg, 20 mg, 30 mg, 40 mg or 50 mg of a steroid, such as a glucocorticoid.

In one embodiment, the oral composition can comprise about 50 mg to about 500 mg of abiraterone acetate and an amount of about 0.25 mg to about 3.5 mg of the steroid, such as hydrocortisone, prednisone or dexamethasone. In other instances, the composition can comprise about 50 mg to about 300 mg of abiraterone acetate and an amount of about 1.0 mg to about 2.5 mg of the steroid, such as hydrocortisone, prednisone or dexamethasone. In another embodiment the composition can comprise about 50 mg to about 300 mg of abiraterone acetate and about 0.5 mg to about 3.0 mg of a steroid. For example, the oral composition can be a tablet containing 250 mg of abiraterone acetate; 1.25 mg or 2.0 mg of a steroid, such as hydrocortisone, prednisone or dexamethasone; and one or more carriers, excipients, diluents or additional ingredients. Additionally, the oral composition can be a capsule containing 250 mg of abiraterone acetate; 1.25 mg or 2.0 mg of a steroid, such as hydrocortisone, prednisone or dexamethasone; and one or more carriers, excipients, diluents or additional ingredients.

The description contained herein is for purposes of illustration and not for purposes of limitation. The methods and compositions described herein can comprise any feature described herein either alone or in combination with any other feature(s) described herein. Changes and modifications may be made to the embodiments of the description. Furthermore, obvious changes, modifications or variations will occur to those skilled in the art. Also, all references cited above are incorporated herein, in their entirety, for all purposes related to this disclosure.

What is claimed is:

1. A method for the treatment of a prostate cancer in a human comprising administering to said human a therapeutically effective amount of abiraterone acetate or a pharmaceutically acceptable salt thereof and a therapeutically effective amount of prednisone.

2. The method of claim 1, wherein the therapeutically effective amount of the abiraterone acetate or pharmaceutically acceptable salt thereof is from about 50 mg/day to about 2000 mg/day.

3. The method of claim 2, wherein the therapeutically effective amount of the abiraterone acetate or pharmaceutically acceptable salt thereof is from about 500 mg/day to about 1500 mg/day.

4. The method of claim 3, wherein the therapeutically effective amount of the abiraterone acetate or pharmaceutically acceptable salt thereof is about 1000 mg/day.

5. The method of claim 1, wherein the therapeutically effective amount of the abiraterone acetate or a pharmaceutically acceptable salt thereof is administered in at least one dosage form comprising about 250 mg of abiraterone acetate or a pharmaceutically acceptable salt thereof.

6. The method of claim 1, wherein the therapeutically effective amount of the prednisone is from about 0.01 mg/day to about 500 mg/day.

7. The method of claim 6, wherein the therapeutically effective amount of the prednisone is from about 10 mg/day to about 250 mg/day.

8. The method of claim 7, wherein the therapeutically effective amount of the prednisone is about 10 mg/day.

9. The method of claim 1, wherein the therapeutically effective amount of the prednisone is administered in at least one dosage form comprising about 5 mg of prednisone.

10. The method of claim 1, comprising administering to said human about 500 mg/day to about 1500 mg/day of abiraterone acetate or a pharmaceutically acceptable salt thereof and about 0.01 mg/day to about 500 mg/day of prednisone.

11. The method of claim 10, comprising administering to said human about 1000 mg/day of abiraterone acetate or a pharmaceutically acceptable salt thereof and about 10 mg/day of prednisone.

12. The method of claim 1, wherein said prostate cancer is refractory prostate cancer.

13. The method of claim 12, wherein the refractory prostate cancer is not responding to at least one anti-cancer agent.

14. The method of claim 13, wherein the at least one anti-cancer agent comprises a hormonal ablation agent, an anti-androgen agent, or an anti-neoplastic agent.

15. The method of claim 14, wherein the hormonal ablation agent comprises deslorelin, leuprolide, goserelin, or triptorelin.

16. The method of claim 14, wherein the anti-androgen agent comprises bicalutamide, flutamide, or nilutamide.

17. The method of claim 14, wherein the anti-neoplastic agent comprises docetaxel.

18. The method of claim 12, comprising administering to said human about 500 mg/day to about 1500 mg/day of abiraterone acetate or a pharmaceutically acceptable salt thereof and about 0.01 mg/day to about 500 mg/day of prednisone.

19. The method of claim 18, comprising administering to said human about 1000 mg/day of abiraterone acetate or a pharmaceutically acceptable salt thereof and about 10 mg/day of prednisone.

20. The method of claim 17, comprising administering to said human about 1000 mg/day of abiraterone acetate or a pharmaceutically acceptable salt thereof and about 10 mg/day of prednisone.

* * * * *